United States Patent [19]

Tosi et al.

[11] Patent Number: 5,176,911
[45] Date of Patent: Jan. 5, 1993

[54] PHARMACEUTICAL COMPOSITIONS COMPRISING SELECTED LACTOBACILLUS STRAINS

[75] Inventors: Silvana Tosi; Giancarla Dondi; Vittorio Bottazzi; Franco Dellaglio; Lorenzo Morelli, all of Novara, Italy

[73] Assignees: Universita Cattolica del Sacro Cuore, Milan; Dr. A. Tosi Farmaceutici S.r.l., Novara, both of Italy

[21] Appl. No.: 388,479

[22] Filed: Aug. 2, 1989

[30] Foreign Application Priority Data

Aug. 5, 1988 [IT] Italy ............................ 21663 A/88

[51] Int. Cl.⁵ .......................... C12N 1/20; C12R 1/25; A61K 35/66
[52] U.S. Cl. ................................ 424/93 J; 435/252.9
[58] Field of Search ............... 435/252.9; 424/93, 93 J

[56] References Cited

U.S. PATENT DOCUMENTS 4,689,226  8/1987  Nurmi et al. ............... 435/252.9
4,839,281  6/1989  Gorbach et al. ................. 424/93

FOREIGN PATENT DOCUMENTS 8404675 12/1984 World Int. Prop. O. ........... 424/93

OTHER PUBLICATIONS

Bergey's Manual of Systematic Bacteriology, vol. 2 (1986), pp. 1218-1224, 1226-1228, and 1232.
Wood, Biosis, vol. 81: 63689 (1985).

Primary Examiner—Jacqueline Stone
Attorney, Agent, or Firm—Griffin Butler Whisenhunt Kurtossy

[57] ABSTRACT

Topical pharmaceutical compositions, suited for the use in gynecology and urology, comprise as active principles selected Lactobacillus strains isolated from vaginal or urologic habitat of asymptomatic patients.

5 Claims, No Drawings

PHARMACEUTICAL COMPOSITIONS COMPRISING SELECTED LACTOBACILLUS STRAINS

The present invention concerns pharmaceutical compositions suited for the treatment of vaginal and urological diseases, containing selected strains of microorganisms of the "Lactobacillus" genus.

A further object of the invention is provided by said strains.

The use of lactic acid bacteria in gynecology has already been proposed (FR 6838 M and U.S. Pat. No. 4592748).

Their use in urology has been disclosed, for instance, by:

a) Andrew W. BRUCE—Gregor REID: "Intravaginal instillation of lactobacilli for prevention of recurrent urinary tract infections";

b) Gregor REID—Andrew W. BRUCE—Mojtaba BEHESATI: "Effect of antibiotic treatment on receptivity of uroepithelial cells to uropathogens";

c) Gregor REID—Jacqueline A. McGROARTY—Rosanne ANGOTTI and Roger L. COOK: "Lactobacillus inhibitor production against "Escherichia coli" and coaggregation ability with uropathogens".

It has now been found that the use of particular strains of Lactobacillus, isolated from the vaginal habitat, taxonomically characterized and selected by means of "in vitro" activity tests, allow to obtain particularly favourable therapeutic results, thanks to:

(a) their high affinity towards the vaginal epithelium allowing their implant on the vaginal mucosa both in physiological and in pathological conditions, restoring therefore the optimal microflora and pH conditions;

(b) their direct action on the pathogenic microorganism, apparently not due to the production of diffusible inhibitory substances but to a coaggregation with the phatogenic microorganism.

Of course, the validity of the invention should not be considered to be connected with the verification of the above suggested mechanism of action.

The pharmaceutical compositions of the invention are particularly useful for the treatment of vaginal and urological infections of mycotic and bacterial origin.

The strains were deposited at the Collection National de Cultures de Microorganisms (CNCM) of Institut Pasteur—Paris (France) on Jul. 21, 1988;

The identity and deposit numbers of the strains of the invention is hereinbelow reported.

| | |
|---|---|
| LACTOBACILLUS CASEI | I-785 |
| LACTOBACILLUS GASSERI | I-786 |
| LACTOBACILLUS FERMENTUM | I-789 |
| LACTOBACILLUS CASEI SUBSP.PSEUDOPLANTARUM | I-790 |
| LACTOBACILLUS CRISPATUS | I-787 |
| LACTOBACILLUS FERMENTUM | I-788 |

Some information relevant to the characterisation of the strain of the invention are hereinbelow reported.

Lactobacillus Casei: I-785

Guanine+cytosine content (G+C %): 39.7%

Fermented sugars according to API CHL 5041 test

L-arabinose
ribose
galactose
glucose
fructose
N-acetylglucosamine
maltose
melibiose
sucrose
melicitose
raffinose
gluconate
5-oxo-gluconate
  Plasmids: 1 plasmid 30M daltons
  Surface protein (S-layer): Molecular weight 56-66.000 daltons.

*Lactobacillus gasseri*: I-786

G+C %: 34.5

Fermented sugars according to API CHL 5041 test galactose
glucose
fructose
mannose
N-acetylglucosamine
amygdaline
arlutine
salicine
cellobiose
maltose
sucrose
trehalose
gentiliose
D tagatose
  Plasmids: 1 32M daltons
  Surface protein: two bands with Molecular weight = 50.000
  Hybridization with *Lactobacillus gasseri* DSM 20043:78%

*Lactobacillus fermentum*: I-789

G+C %: 51.2

Fermented sugar according to HPI CHL 5041 test

L-arabinose
ribose
galactose
glucose
fructose
mannose
maltose
lactose
melibiose
sucrose
raffinose
gluconate
5-oxo-gluconate
  Hybridization with *Lactobacillus fermentum* ATCC 14932:100%

*Lactobacillus casei* supsp.Pseudoplantarum: I-790

G+C %: 46
Hybridization with ATCC 2558:92%

*Lactobacillus crispatus*: I-787

G+C %: 38
Hybridization with ATCC 33820:80%

*Lactobacillus fermentum* (LF4): I-788

G+C %: 52.2

Hybridization with ATCC 14931

The compositions of the invention may comprise one or more strains selected in the above defined group.

Particularly favourable therapeutic results were obtained with the following mixtures:

MIXTURE A 1

| | |
|---|---|
| *Lactobacillus Casei* | I-785 |
| *Lactobacillus Gasseri* | I-786 |
| *Lactobacillus Fermentum* | I-789 |

MIXTURE A 2

| | |
|---|---|
| *Lactobacillus Casei* subsp.Pseudoplantarum | I-790 |
| *Lactobacillus Crispatus* | I-787 |
| *Lactobacillus Fermentum* | I-788 |

Of course, other mixtures or single strains may be advantageously used in the compositions, comprised within the invention's scope.

A particularly preferred strain is *Lactobacillus fermentum* I-789, which proved to be endowed with a direct inhibitory action on some species of pathogenic fungi, particularly on Candida strains, as it has been shown by means of in vitro tests on agar plates whereupon Candida strain was contacted with *Lactobacillus fermentum* I-789. An inhibitory halo of Candida was noticed and a test carried out using the sterile surnatant of the I-789 culture instead of the whole cells shows that said inhibitory action is not due to inhibitory substances released in the culture medium.

For the practical use, the microorganisms of the invention are formulated in suitable administration forms such as ovules, creams, vaginal capsules, solutions for lavages, sachets and the like. Unit doses may comprise from $10^3$ to $10^{10}$ cells of each single strain, the preferred dosage being about $10^6$ cells per unit dose.

The bacterial cultures are preferably in lyophilized forms and may be prepared according to conventional methods.

For the preparation of aqueous formulations for lavages and irrigations small bottles are used, provided with resevoirs containing the lyophilized microorganisms, to be dissolved before use in a suitable liquid carrier contained in the bottles.

The compositions of the invention are practically devoid of any toxicity and show no systemic absorptions so as to allow the administration also to pregnant patients and in cases of intolerability to antimycotic or antibacterial drugs.

The compositions of the invention are therefore particularly useful, inter alia, for the prophylaxis of fungal infections due to antibiotic treatments and corresponding complications (formation of resistant strains, relapses etc.). The clinical experience up to now acquired shows as particularly convenient and effective a treatment schedule comprising the administration of the composition of the invention in form of capsules, creams or ovules to be administered before sleeping followed by a lavage on the subsequent morning.

The following non limitative examples further illustrate the compositions of the invention.

EXAMPLE 1

| OVULES | |
|---|---|
| Active principle Mixture A 1 | $1 \times 10^6$ cells of each strain |
| Excipient Semi-synthetic glycerides | 2800 mg |

EXAMPLE 2

| VAGINAL CREAM (30 g tube) | |
|---|---|
| Active principle *Lactobacillus fermentum* I-789 | $1 \times 10^6$ cells of each strain |
| Excipient | |
| Hydrogenated lanoline | 5 g |
| Vaseline oil | 5 g |
| Dimethylpolysiloxane | 10 g |
| SiO₂ (Aerosil 200 ®) | 15 g |
| Dodecylglycol | 1.5 g |
| polyethylenglycol 1000 copolymer | 6 g |

EXAMPLE 3

| VAGINAL CAPSULES | |
|---|---|
| Active principle Mixture A 1 | $1 \times 10^6$ cells of each strain |
| Excipient | |
| Triglycerides with $C_8$–$C_{12}$ fatty acids (Miglio) ® | 1500 mg |
| Glycerine | 2500 mg |
| Titanium dioxide | 10 mg |

EXAMPLE 4

| BOTTLES WITH RESERVOIR Each bottle contains: | |
|---|---|
| a) RESERVOIR Lyophilized mixture A 1 | $1 \times 10^6$ cells of each strain |
| b) BOTTLE (10 ml) | |
| Glycerine | 4.0 g |
| Water q.s. to | 10 ml |

EXAMPLE 5

| SOLUTION FOR LAVAGES Each bottle with reservoir contains: | |
|---|---|
| a) RESERVOIR Lyophilized mixture A 2 | $1 \times 10^3$ cells of each strain |
| b) BOTTLE (150 ml) | |
| Glycerine | 60 g |
| Water q.s. to | 150 ml |

We claim:

1. A strain of Lactobacillus, deposited at C.N.C.M. of Institute Pasteur and having the identity and deposit number of *Lactobacillus fermentum* I-789.

2. A pharmaceutical composition containing the Lactobacillus strain of claim 1.

3. A pharmaceutical composition according to claim 2 containing from $10^3$ to $10^{10}$ cells of the strain per unit dose.

4. A pharmaceutical composition according to claim 4 containing about $10^6$ cells of each strain per unit dose.

5. A pharmaceutical composition according to claim 2 in the form of creams, ovules, vaginal capsules, or solutions for lavages.

* * * * *